(12) United States Patent
Heckel et al.

(10) Patent No.: US 9,012,146 B2
(45) Date of Patent: Apr. 21, 2015

(54) METHOD FOR SELECTIVELY ENRICHING AND ISOLATING MICROBIAL AND OPTIONALLY ADDITIONAL VIRAL NUCLEIC ACIDS

(75) Inventors: Dirk Heckel, Saint Martin d'Uriage (FR); Thomas Doedt, Hilden (DE)

(73) Assignee: QIAGEN GmbH, Hilden (DE)

( * ) Notice: Subject to any disclaimer, the term of this patent is extended or adjusted under 35 U.S.C. 154(b) by 0 days.

(21) Appl. No.: 13/510,525

(22) PCT Filed: Nov. 19, 2010

(86) PCT No.: PCT/EP2010/067787
§ 371 (c)(1),
(2), (4) Date: May 17, 2012

(87) PCT Pub. No.: WO2011/061274
PCT Pub. Date: May 26, 2011

(65) Prior Publication Data
US 2012/0231446 A1    Sep. 13, 2012

(30) Foreign Application Priority Data

Nov. 19, 2009  (EP) .................................... 09014446

(51) Int. Cl.
| | | |
|---|---|---|
| *C12Q 1/68* | (2006.01) | |
| *C12Q 1/70* | (2006.01) | |
| *G01N 33/53* | (2006.01) | |
| *G01N 33/567* | (2006.01) | |
| *C07H 21/02* | (2006.01) | |
| *B01L 3/00* | (2006.01) | |
| *C12N 15/10* | (2006.01) | |

(52) U.S. Cl.
CPC .................................. *C12N 15/1003* (2013.01)

(58) Field of Classification Search
USPC ............. 435/5, 6.1, 6.15, 7.2, 7.23; 536/23.1; 422/430
See application file for complete search history.

(56) References Cited

U.S. PATENT DOCUMENTS

| 7,255,989 B1 * | 8/2007 | Jeannin et al. ................. 435/6.1 |
| 7,893,251 B2 | 2/2011 | Lorenz |

FOREIGN PATENT DOCUMENTS

| DE | 10 2005 009 479 A1 | 9/2006 |
| WO | 2009/144182 A1 | 12/2009 |

OTHER PUBLICATIONS

Corinaldesi et al, Simultaneous Recovery of Extracellular and Intracellular DNA Suitable for Molecular Studies from Marine Sediments, 2005, Applied and Environmental Microbiology, 71, 46-50.*
Ascher et al, Sequential extraction and genetic fingerprinting of a forest soil metagenome, 2009, Applied Soil Ecology, 42, 176-181.*
Tzeneva et al, Effect of soil sample preservation, compared to the effect of other environmental variables, on bacterial and eukaryotic diversity, 2009, Research in Microbiology, 160, 89-98.*
Kellermayer et al., "Release of Potassium, Lipids, and Proteins From Nonionic Detergent Treated Chicken Red Blood Cells," *Journal of Cellular Physiology 159*:197-204, 1994.

* cited by examiner

Primary Examiner — Narayan Bhat
(74) Attorney, Agent, or Firm — Seed IP Law Group PLLC (57) ABSTRACT

The present invention relates to a method for selectively enriching and/or isolating microbial and optionally additionally viral nucleic acids from samples that contain a mixture of microbial cells, freely circulating nucleic acids and higher eukaryotic cells, and optionally additionally viruses, in a liquid, and to a kit for selectively enriching and/or isolating intracellular and extracellular microbial nucleic acids, and optionally additionally viral nucleic acids, from samples that contain a mixture of microbial and higher eukaryotic cells, freely circulating nucleic acids, in particular extracellular microbial nucleic acids, and optionally additionally viruses in a liquid.

53 Claims, 3 Drawing Sheets

METHOD FOR SELECTIVELY ENRICHING AND ISOLATING MICROBIAL AND OPTIONALLY ADDITIONAL VIRAL NUCLEIC ACIDS

The present invention relates to a method for selectively accumulating and/or isolating microbial and, optionally and additionally, viral nucleic acids from samples which comprise a mixture of microbial cells, higher eukaryotic cells and free-circulating nucleic acids and also, optionally, viruses in a liquid, and also to a kit for selectively accumulating and/or isolating more particularly intracellular and also extracellular microbial and, optionally and additionally, viral nucleic acids from samples which comprise a mixture of microbial and higher eukaryotic cells, free-circulating nucleic acids, more particularly extracellular microbial nucleic acids, and possibly also viruses in a liquid.

Analytical and diagnostic methods of molecular biology are becoming increasingly important, more particularly in human medicine or veterinary medicine for detecting infections or genetic dispositions to disease, since they, in contrast to conventional methods, enable a very fast detection of the pathogens and thus a fast diagnosis. The latter in turn enables the start of a targeted therapy at an early stage and can therefore, more particularly in the case of life-threatening infections, decisively lower the mortality rate of the patients. Thus, by way of example, the fatality rate for sepsis patients is currently still in the range from 20 to 50%, and sepsis is the most common cause of death of people admitted to a hospital. This circumstance is not least a result of the comparatively lengthy diagnostic methods, which inevitably delay the start of therapy. Traditionally, detection of infections of this kind is achieved by culturing samples acquired from the patients, the samples containing the pathogen(s), under suitable conditions, i.e. growing them on a suitable culture medium, so that a multiplication of the microorganisms is attained and, subsequently, the corresponding colonies can be detected. This cultivation method generally requires, however, several days (about 3 to 7 days). Furthermore, numerous pathogens cannot be detected through setting up blood cultures. This applies more particularly to virus diagnostics.

Modern diagnostic methods therefore concentrate on the specific detection of the pathogenic nucleic acids (deoxyribonucleic acids/DNA and/or ribonucleic acids/RNA). Since the polymerase chain reaction (PCR) makes it possible, within a few hours, to exponentially multiply even very low amounts of nucleic acids, this approach enables the detection of microbial DNA in human blood samples with enormous time savings, for example in sepsis diagnosis, and can decisively improve the chances of survival of the afflicted patients.

Depending on the type of pathogen, the greatest proportion of the nucleic acids to be detected is located in the interior of a cell ("intracellular nucleic acids") or else freely circulating in the infected sample ("extracellular nucleic acids"). In order to be able to isolate the intracellular nucleic acids, these nucleic acids first need to be released from the cells before they can be purified, multiplied using PCR techniques and/or analysed. A further problem in the detection of microbial DNA from samples which comprise a mixture of microbial cells and higher eukaryotic cells, such as, for example, blood samples from patients with sepsis, is also the fact that a lysis of the cells releases not only the microbial nucleic acids to be analysed from the microbial cells present in the sample but also large amounts of the eukaryotic nucleic acids from the higher eukaryotic cells, whose number in a sample acquired from a higher eukaryote is generally a multiple of the number of microbial cells. Nucleic acid preparations which are acquired from mixed samples of this kind thus comprise a mixture of nucleic acids of all cell types present in the sample. The average ratio of microbial to human DNA in blood samples from human sepsis patients is about 1 to $2 \times 10^9$, and thus the subsequent amplification methods for detecting the microbial DNA quite often result in the formation of non-specific amplification products which can complicate a subsequent diagnosis or even lead to misdiagnoses.

In the prior art, there were already various approaches to circumvent this problem through a suitable method for cell disruption (cell lysis) of the cells present in such a sample. For instance, WO 2006/092278 A1 describes a method which makes possible the selective isolation of microbial nucleic acids from a mixed sample which comprises not only microbial cells but also higher eukaryotic cells. The higher eukaryotic cells naturally present in large numbers in a human blood sample are disrupted using a mild lysis buffer which comprises a chaotropic agent at a relatively low concentration, whereas the microbial cells also present in the tested samples initially remain intact. The method takes advantage of the fact that microbial cells are more stable in comparison with eukaryotic cells under chaotropic conditions. The lysate obtained, which comprises the eukaryotic cell constituents released by the lysis and also the intact microbial cells, subsequently receives an addition of a suitable nuclease which degrades the eukaryotic DNA, whereas the intracellular microbial DNA is protected from digestion in the intact microbial cell. Through subsequent centrifugation, the microbial cells can be removed as a pellet from the lysate, which comprises the (at least partially) degraded eukaryotic DNA. In a next step, the microbial cells obtained in this way are subjected to further disruption to release the microbial intracellular DNA. A disadvantage of this method, however, is that viral nucleic acids and the free-circulating nucleic acids, more particularly the extracellular microbial nucleic acids, which are present in the liquid constituent of the sample, in the case of blood samples, for example in blood plasma, are inevitably lost due to the preceding nuclease digestion. This is more particularly a disadvantage with regard to newer findings which have shown that nucleic acids present in plasma, more particularly free-circulating nucleic acids, are important prognostic markers (A. Rhodes et al., *Critical Care* 2006, 10:R60). More particularly in a sepsis, the patients exhibit a strongly increased content of free-circulating nucleic acids in blood plasma, and said content can be used as an independent indicator for predicting the disease progression and the mortality of the patient (see, for example, M. E. Bougnoux et al. *J. Clin. Microbiol.* 1999, 37, 925-930; L. Metwally et al. *J. Med. Microbiol.* 2008, 57, 1269-1272; K. Saukkonen et al. *Clin. Chem.* 2008, 54 (6), 1000-1007; Y. K. Tong et al. *Clin. Chim. Acta* 2006, 363 (1-2), 187-196).

WO 2009/015484 A1 also describes a method for isolating microbial nucleic acids from body fluids which comprise not only endogenous cells but also microorganisms. The method described therein comprises a two-level lysis method. In a first step, under suitable conditions, the blood cells are selectively lysed, whereas the microbial cells remain intact. Subsequently, the lysed sample is centrifuged in order to remove the intact microbial cells as a pellet. After washing the pellet, the microbial nucleic acids can be released from the microbial cells present in this pellet through further lysis. Methods based on a similar principle for isolating microbial cells from biological samples which comprise mixed samples of this kind of microbial and higher eukaryotic cells are also described in WO 97/07238 A2, WO 2006/088895 A2 and WO 2008/017097 A1. The methods described therein, however, do not mention even one means for isolating the extracellular microbial DNA.

A further approach for separating intracellular microbial DNA from human DNA from whole blood mixed samples underlies the VYOO kit from SIRS-Lab (Jena, Germany). After a mechanical lysis of the different cells present in a mixed sample, the total DNA of the sample is first isolated. The microbial DNA in the sample is accumulated in a next step by means of a solid-phase-bound antibody which binds the unmethylated DNA of the microbial pathogens, whereas the methylated human DNA is not bound. In a subsequent step, the bound microbial DNA must be eluted from the solid phase and finally precipitated from the eluate obtained. Using this method, both intracellular and extracellular microbial nucleic acids can be accumulated, but accumulation by means of binding to the antibody-functionalized solid phase is not quantitative, and significant amounts of the microbial DNA are also lost in the subsequent precipitation. A further disadvantage is that viral nucleic acids are not purified in this method either. In addition, the method is extremely time consuming.

Accordingly, an object of the present invention was to provide a method for selectively accumulating and/or isolating microbial nucleic acids from samples which comprise a mixture of microbial cells and higher eukaryotic cells and also free-circulating nucleic acids in a liquid, with the method allowing the accumulation and/or isolation of both intracellular and extracellular, more particularly microbial, nucleic acids from the same sample in a short time.

This object is achieved by the method according to the invention. The invention therefore provides a method for selectively accumulating and/or isolating microbial nucleic acids from samples which comprise a mixture of microbial cells and higher eukaryotic cells and also free-circulating nucleic acids, more particularly extracellular microbial nucleic acids, in a liquid, with the method comprising the following steps:
1. substantially separating the liquid constituent of the sample, including the substances dissolved in this liquid constituent, such as the free-circulating nucleic acids, more particularly the extracellular nucleic acids, from the solid constituents of the sample, more particularly from the cellular constituents,
2. selectively lysing the eukaryotic cells present in the solid sample constituents without simultaneously lysing the microbial cells,
3. substantially separating the solid constituents, including the microbial cells, from the liquid constituent, including the substances dissolved in this liquid constituent, of the lysate obtained in step 2,
4. resuspending the solid constituents obtained in step 3,
5. lysing the microbial cells which are present in the suspension obtained in step 4,
6. purifying and/or concentrating the free-circulating, more particularly the extracellular microbial, nucleic acids from the liquid constituent obtained in step 1 and/or the intracellular microbial nucleic acids from the lysate obtained in step 5.

Provided that the sample comprises not only the microbial and the higher eukaryotic cells and the free-circulating nucleic acids but also viruses, it is also optionally possible, additionally or else simultaneously in step 6, to accumulate and/or isolate the viral nucleic acids, since the viruses should be present mainly in the liquid constituent of the sample, removed in step 1 of the method, and can be therefore likewise effectively removed from the higher eukaryotic cells.

Particularly preferably, according to step 6 of the present method, both the extracellular and the intracellular, more particularly microbial, nucleic acids are purified. This can be carried out simultaneously or separately, one after another, or after combining the liquid constituent from step 1 with the lysate from step 5.

Using the method according to the invention, both intracellular and extracellular microbial nucleic acids can be isolated and accumulated from mixed samples which comprise not only the microbial cells but also higher eukaryotic cells and free-circulating nucleic acids. It is possible to purify and to concentrate the intracellular nucleic acids and/or the extracellular nucleic acids independently of one another or together after combining the corresponding fractions. If desired, the method also makes possible, in addition to selective accumulation and/or isolation of the microbial nucleic acids, selective accumulation and/or isolation of the higher eukaryotic nucleic acids. The nucleic acids to be isolated can be both RNA and DNA, each of which can be single-stranded or double-stranded. While, for the detection of microbial cells, the nucleic acids preferably are DNA, both DNA and RNA are of interest for the detection of viruses, depending on the type of virus (DNA or RNA virus).

The nucleic acids obtained with the method according to the invention can be subsequently detected by highly specific and sensitive methods, such as PCR reactions and/or hybridization reactions. Owing to the depletion of the human gDNA, very high input volumes can be used, and the bound nucleic acids eluted simultaneously in very small elution volumes. This high ratio of input volume to elution volume thus results in a very high sensitivity. Without the depletion of the human gDNA, the input/elution ratio would not be possible, since subsequently PCR inhibitions could occur. The method also makes possible even the release and the detection of phagocytized microbial cells from granulocytes or macrophages.

For the purposes of the present invention, the term "selective accumulation and/or isolation" is understood to mean a method which makes it possible to provide nucleic acids in a reproducible manner from a mixed sample which comprises microbial cells, free-circulating nucleic acids, possibly viruses and higher eukaryotic cells, with said nucleic acids originating exclusively or predominantly from the microbial cells present in the sample, and including the extracellular microbial nucleic acids, and also, additionally, any nucleic acids of viral origin, while the proportion of the nucleic acids from higher eukaryotic cells in the sample is, at the same time, distinctly reduced.

Higher eukaryotic cells are understood to mean, for the purposes of the invention, eukaryotic cells of a higher evolutionary level, such as those which occur, for example, in plant or animal organisms. Multicellular organisms of this kind feature, inter alia, cell differentiation, in which the single higher eukaryotic cell does not perform by itself all biochemical and metabolic functions essential for life, but has adapted through specialization to performing one or more functions. The term higher eukaryotic cell in this context comprises both cells which are organized in a tissue and individual cells, for example spermatozoa or blood cells, which occur in the body fluids of a mammal, including humans, or in its excretory products, for example in blood, lymph fluid, cerebrospinal fluid, in urine, faeces or saliva. Preferably, the higher eukaryotic cells are mammalial cells, particularly preferably human cells. Suspensions or slurries of samples in an aqueous solution, for example a buffer, can also serve as starting material for the present method.

The sample to be analysed comprises a mixture of microbial cells, free-circulating nucleic acids, more particularly extracellular microbial nucleic acids, possibly viruses and higher eukaryotic cells in a fluid. Preferably, the sample originates from a natural environment, for example from a plant, animal or human organism. Preferably, the sample is body fluids from mammals, particularly preferably from humans, comprising punctates, cerebrospinal fluid, lymph fluid, synovial fluid, peritoneal fluid or pleural fluid, bone marrow, blood, more particularly whole blood, sperm, urine, faeces, saliva and bronchoalveolar lavage, concentrates or diluted solutions thereof or resuspended cell material which was acquired via swabs. Particularly preferably, the sample is blood or blood concentrates, such as thrombocyte concentrates or erythrocyte concentrates.

Microbial cells, for the purposes of the invention, refer to the diverse group of organisms which exist in nature on their own as a single cell or as a cell cluster and thus differ from higher eukaryotic cells, which do not occur in nature as single cells but exclusively as constituents of multicellular organisms having cell specialization. The term "microbial cell" is, for the purposes of the invention, understood to mean, inter alia, prokaryotic cells, for example bacteria or archaebacteria, but also cells of lower eukaryotes, such as microscopic algae, yeasts, fungi or protozoa. In a preferred embodiment, the microbial cells are bacterial cells and/or cells of lower fungi.

The term "bacteria" here comprises gram-positive and gram-negative bacteria, more particularly bacteria of the genera *Mycobacterium* spp., *Enterococcus, Enterobacter, Klebsiella, Proteus, Pseudomonas, Serratioa, Escherichia, Acinetobacter, Streptococcus, Staphylococcus, Salmonella, Legionella, Chlamydia, Shigella, Pseudomonas, Listeria, Yersinia, Corynebacterium, Bordetella, Bacillus, Clostridium, Haemophilus, Helicobacter* and *Vibrio*.

Fungal cells whose nucleic acids can be accumulated and/or isolated with the method according to the invention are, more particularly, cells from fungi of the genera *Aspergillus, Basidiobolus, Cephalosporium, Skopulariopsis, Rhizomucor, Entomophthora, Mucor, Syncephalastrum, Absidia, Altenaria, Rhizopus, Stemphylium, Nigrospora, Chrysosporium, Botrytis, Helmithosporium, Curvularia, Hemispora, Phoma, Paecilomyces* and *Thielavia*, more particularly *A. fumigatus, A. tereus, A. niger, A. nidulans, A. homegadus, A. flavus B. microsporus, B. rhanarum, C. crysogenum, C. corebiobides, C. regatum* and *C. diospyri*.

In addition, the nucleic acids of the pathogenic yeasts of the genus *Candida*, for example *C. tropicalis, C. glabrata, C. krusei, C. parapsilosis, C. albicans, C. guiffiermondii* and others can also be accumulated and/or isolated, similarly the nucleic acids from algae, for example from *Euglena* spp., *Coscinodiscus* spp., *Trachelomonas* spp., *Gymnodinium sanguineum, Dinophysis nitra, Ceratium massiliense, Chlorella, Chlorococcum* or *Eremosphaera*, or from protozoa, such as, for example, *Plasmodium, Trypanosoma, Leishmania, Toxoplasma* and *Cryptosporidium*, preferably *Plasmodium malariae, Plasmodium falciparum, Trypanosoma brucei, Trypanosoma cruzei, Toxoplasma gondii, Cryptosporidium parvum, Cryptosporidium serpentis* and *Cryptosporidium hominis*.

Furthermore, viral nucleic acids can also be optionally accumulated and/or isolated by the method according to the invention, such as, for example, preferably the DNA of the hepatitis B virus (HBV), the Epstein-Barr virus (EBV) and the cytomegalovirus (CMV) and/or the RNA of the human immunodeficiency virus (HIV) and the hepatitis C virus (HCV).

The method according to the invention is not restricted to a particular sample volume, and both sample volumes in the μl range and distinctly larger sample volumes of, for example, 50 or 100 ml can be processed, with the below-mentioned amounts and volumes of the agents and solutions used in the method, and likewise the duration of the individual procedural steps, being then appropriately adapted to the sample amount, if appropriate in accordance with standards known to a person skilled in the art. Preferably, the volume of the sample is in the range from 1 to 20 ml, more preferably from 2 to 15 ml and particularly preferably from 3 to 8 ml.

The liquid constituents, including the substances dissolved in these liquid constituents, such as, for example, free-circulating nucleic acids and, additionally, any viruses present in the sample, can be separated from the solid constituents in procedural steps 1 and 3 of the method according to the invention by, for example, filtration, centrifugation or decantation. The liquid constituents can be separated from the solid constituents in procedural step 1 by the same method as in procedural step 3 or by a different one. Preferably, the liquid constituents are separated from the solid constituents in procedural steps 1 and/or 3 of the method according to the invention in accordance with the methods known in the prior art for acquiring plasma from whole blood samples by means of centrifugation of the sample. The sample is preferably centrifuged for from 2 to 30 minutes, more preferably for from 5 to 20 minutes and particularly preferably for from 10 to 15 minutes. The sample is preferably centrifuged at an acceleration in the range from 2000 to 10,000 g, preferably at 5000 g. If the liquid constituents are separated from the solid constituents both in procedural step 1 and in procedural step 3 of the method according to the invention by means of centrifugation of the sample, the acceleration and the duration of the centrifugation can be the same or different in the two procedural steps. For instance, when processing a whole blood sample, the plasma, including the nucleic acids, more particularly microbial nucleic acids, freely circulating in the plasma and, if present, the viruses, can be removed from the solid sample constituents, more particularly the blood cells and the microbial cells, in a first procedural step by centrifugation at 5000 g±500 g for 10 minutes. After removal of the supernatant of the centrifuged sample and subsequent selective lysis of the eukaryotic cells present in the solid sample constituents, i.e. in the pellet, without simultaneous lysis of the microbial cells, the liquid constituent obtained in this step (the lysate), including the substances dissolved in this liquid constituent, more particularly the released eukaryotic cell constituents, can be separated from the solid constituents, including the microbial cells, by a further centrifugation step, for example at 5000±500 g for 15 minutes.

The supernatant can be removed from the solid constituents after the centrifugation by any method known to a person skilled in the art for this purpose, for example by decanting or pipetting off the supernatant.

The selective lysis of the eukaryotic cells in procedural step 2 of the method according to the invention is preferably carried out in a mixture (Buffer 1) which comprises 1. at least one chaotropic substance, preferably selected from the group comprising guanidinium thiocyanate (GTC), guanidinium hydrochloride (GuHCl), guanidinium isothiocyanate (GIT), alkali perchlorates, alkali iodides, urea and mixtures thereof,
2. at least one surfactant, preferably a non-ionic surfactant, particularly preferably selected from the group comprising sorbitan esters of fatty acids, polyoxyethylene sorbitan esters of fatty acids, polyoxyalkylene ethers of fatty acid alcohols, polyoxyalkylene ethers of alkylphenols, poloxamers and mixtures thereof and 3. at least one buffer substance, preferably selected from the group comprising Tris, MES, MOPS, HEPES and mixtures thereof.

The term "lysis" is, for the purposes of the invention, understood to mean a method for at least partial disruption of cells with at least partial destruction of the membranes and/or cell walls which enclose the nucleic acids of the cells and separate them from the surrounding medium. The at least partial destruction of these structures releases the cell constituents, such as proteins and nucleic acids, into the surrounding liquid. Selective lysis of the higher eukaryotic cells, for the purposes of the invention, refers to a method in which only the higher eukaryotic cells, but not the microbial cells, in a mixed sample are lysed, and thus, after lysis has taken place, only the intracellular nucleic acids of the eukaryotic cells are present in the mixture, whereas the intracellular nucleic acids of the microbial cells continue to be protected by the cell wall enclosing them. Preferably, in this step of selective lysis, more than 50%, more preferably more than 75%, even more preferably more than 90% and most preferably more than 98% of the higher eukaryotic cells present in the sample are lysed, whereas preferably less than 50%, more preferably less than 20%, even more preferably less than 10% and most preferably less than 1% of the microbial cells are lysed. Selective conditions of this kind can be adjusted via, for example, the constituents of the lysis buffers used, the concentration of the constituents in the lysis buffer and the total concentration of the lysis buffer in the sample solution, this being known to a person skilled in the art and elucidated by means of the examples listed later.

Chaotropic substance refers to a chemical compound which has the ability to interfere with the ordered hydrogen bonds in water. Interference of the water structure increases the entropy of an aqueous solution, and the solubility of non-polar substances in this solution is increased. As a result, hydrophobic interactions are minimized, leading to denaturation of proteins and lysis of the cell walls/plasma membranes. The chaotropic substances are found, for example, in the Hofmeister-series. Particularly useful substances are, for example, the previously mentioned guanidinium compounds or else alkali perchlorates, alkali iodides or urea. Preferred alkali perchlorates are, for the purposes of the invention, sodium perchlorate and potassium perchlorate; preferred alkali iodides are sodium iodide and potassium iodide.

A surfactant is, for the purposes of the invention, understood to mean an organic surface-active substance which features at least one hydrophilic and at least one hydrophobic part. For the purposes of the invention, use can be made of anionic surfactants, such as, for example, sodium dodecyl sulphate (SDS), cationic surfactants, such as quaternary tetraalkylammonium salts, for example cetyltrimethylammonium chloride, ampholytic surfactants, such as, for example, 3-[(3-cholamidopropyl)dimethylammonio]-1-propane sulphonate (CHAPS) and non-ionic surfactants or mixtures thereof. Preferably, the surfactant is a non-ionic surfactant or a mixture of various non-ionic surfactants. Particularly preferably, non-ionic surfactants, for the purposes of the invention, are sorbitan esters of fatty acids, such as, for example, sorbitan monooleate, sorbitan sesquioleate, sorbitan trioleate, the corresponding laurates, palmitates, stearates or mixtures thereof, commercially available under, for example, the names Arlacel 83, Span 65, Span 80 or Span 85, polyoxyethylene sorbitan esters of fatty acids, such as, for example, polyoxyethylene sorbitan monooleate, polyoxyethylene sorbitan sesquioleate, polyoxyethylene sorbitan trioleate, the corresponding laurates, palmitates, stearates or mixtures thereof, commercially available under, for example, the names Tween 20 or Tween 85, polyoxyalkylene ethers of fatty acid alcohols, such as, for example, polyoxyethylene lauryl ether, polyoxyethylene stearyl ether, polyoxyethylene cetyl ether, polyoxyethylene oleyl ether or mixtures thereof, for example eicosaethylene glycol hexadecyl ether, commercially available under, for example, the names Brij 58 or Brij 98, polyoxyalkylene ethers of alkylphenols, such as, for example, alkylphenol polyglycol ethers having linear or branched $C_8$-alkyl residues, for example polyethylene glycol [4-(1,1,3,3-tetramethylbutyl)phenyl]ether having 9 to 10 ethylene oxide units, which are commercially available under, for example, the names Triton X-100, Igepal CA-520 or Nonidet P40, and also "poloxamers", block copolymers of ethylene oxide and propylene oxide, commercially available under, for example, the name Pluronic. Preferably, use is made in the above-mentioned substances, independently of one another, medium and higher fatty acids and fatty alcohols, i.e. fatty acids and fatty alcohols having 8-12 and 13-30 carbon atoms, respectively. These fatty acids and fatty alcohols can be saturated or unsaturated. The surfactant facilitates both the miscibility of the individual compounds within the lysis buffer and the miscibility of the lysis buffer with the sample. Furthermore, the surfactant can also actively achieve the destruction of the cell wall structure or plasma membrane structure of the cells.

A buffer substance, for the purposes of the invention, refers to a system of an acid and its conjugated base, which keeps the pH of a solution comprising said buffer substances constant by accepting or releasing protons, depending on whether, in the solution, protons are released or consumed via a reaction or external addition. A buffer substance, for the purposes of the invention, should thus be distinguished from a buffer solution (also referred to as a buffer), which can comprise not only the solvent and the actual buffer substance but also further substances, such as, for example, salts, surfactants and chaotropic agents, etc. For the purposes of the invention, preference is given to buffer substances which stabilize the pH of the buffer solution in the range from 6 to 10, more preferably in the range from 7 to 9, most preferably at 8. For the purposes of the invention, preference is also given to amphoteric buffer substances, i.e. compounds which carry in the same molecule both at least one acidic group and at least one basic group and can thus react both as an acid and as a base.

In a particularly preferred embodiment, Buffer 1 according to the invention is added as Lysis Buffer 1 to the sample to be lysed such that the concentration of the buffer constituents in the sample after addition of the buffer is (1) from 0.1 to 2 M, preferably from 0.2 to 1 M, more preferably from 0.4 to 0.8 M chaotrope, preferably a guanidinium-containing chaotrope as described above, (2) from 0.5 to 5% (w/v), preferably from 1 to 4% (w/v), more preferably from 1.8 to 3% (w/v) surfactant, preferably a non-ionic surfactant and (3) from 2 to 50 mM, preferably from 4 to 30 mM, more preferably 10 mM buffer substance, most preferably at a pH of 8. To reach concentrations of this kind in the lysis solution, use is made in a preferred embodiment of a buffer which has the following concentrations: (1) from 0.2 to 4 M, preferably from 0.4 to 3 M, more preferably 2 M chaotrope, preferably comprising guanidinium, (2) from 0.5 to 10% (w/v), preferably from 1 to 5% (w/v) surfactant, preferably a non-ionic surfactant and (3) from 2 to 100 mM, preferably from 10 to 50 mM buffer substance, preferably at a pH in the range from 6.0 to 10.0, more preferably in the range from 7.0 to 9.0 and most preferably of 8.0.

The separation of the liquid constituents from the solid constituents in procedural step 3 of the method according to the invention, with the separation being preferably achieved by centrifugation, has already been described above. The pellet obtained here, comprising the solid constituents removed from the liquid constituents, in particular the microbial cells, is resuspended in step 4 of the method according to the invention, for example, by briefly shaking the sample in the remaining residual volume of the liquid, after the liquid constituents have been removed, in order to disperse the solid constituents in this liquid. Alternatively, the sample can also be provided with, before or during shaking, a small amount of water, a suitable buffer solution or other suitable solvent. Also, an intermediate step can be introduced in which the pellet is washed in a suitable wash solution, for example, in lysis buffer.

The microbial cells in procedural step 5 of the method according to the invention can, in principle, be lysed using any method which is known to a person skilled in the art and which is suitable for at least partially destroying the cell wall and/or plasma membrane of the microbial cells and releasing the cell constituents present in the cells, more particularly the nucleic acids, into the surrounding liquid. A multiplicity of methods are described in the prior art for various types of microbial cells, such as, for example, repeated thawing and freezing, treatment with enzymes, such as lysostaphin, lyticase or lysozyme, or addition of chemical agents, such as chaotropic substances or surfactants, at an appropriate concentration. Very particularly effective is a combination of various lysis methods which, depending on the compatibility of the means of lysis, can be carried out simultaneously or sequentially. Preferably, the at least partial lysis of the microbial cells in procedural step 5 of the method according to the invention is achieved mechanically. Suitable mechanical methods comprise, for example, the treatment of the microbial cells in a French press, a cell mill or a mortar and also ultrasonication. Particularly preferably, the microbial cells are lysed in procedural step 5 of the method according to the invention through mechanical homogenization of the sample using suitable particles, more particularly beads, preferably glass beads. Here, the mechanical commixing of the sample, comprising the microbial cells and the glass beads, preferably takes place in an instrument which shakes this sample in a horizontal and/or vertical direction, such as, for example, a laboratory vortexer, a QIAGEN Tissue-Lyser, a Fast Prep instrument or the like. Preferably, the mechanical homogenization of the sample is performed in the presence of a buffer solution which can also additionally exhibit lytic properties. In a particularly preferred embodiment, the microbial cells are lysed in procedural step 5 of the method according to the invention by using glass beads of a size in the range from 400 to 600 μm in the presence of a buffer solution, more particularly a buffer having lytic properties.

A buffer solution suitable for use in the above-described mechanical lysis, which additionally exhibits lytic properties (Buffer 2), preferably comprises 1. at least one buffer substance, preferably selected from the group comprising Tris-HCl, MES, MOPS, HEPES and mixtures thereof,
2. at least one complexing reagent for divalent metal ions, preferably EDTA,
3. at least one surfactant, preferably a non-ionic surfactant, particularly preferably selected from the group comprising sorbitan esters of fatty acids, polyoxyethylene sorbitan esters of fatty acids, polyoxyalkylene ethers of fatty acid alcohols, polyoxyalkylene ethers of alkylphenols, poloxamers and mixtures thereof, and
4. optionally a foaming inhibitor, preferably selected from the group comprising Reagent DX (QIAGEN, Hilden, Germany) and SILFOAM® SRE (Wacker Chemie, Munich, Germany) and similar suitable foaming inhibitors, and has a pH in the range from 6 to 10, preferably in the range from 7 to 9, most preferably of 8.

The meaning of the terms buffer substance and surfactant and also preferred embodiments for the purposes of the present invention were already explained above for Lysis Buffer 1. The embodiments mentioned for Buffer 1 are similarly preferred as constituents of Buffer 2, with the non-ionic surfactant used for Buffer 2 particularly preferably being polyoxyalkylene ethers of alkylphenols, such as, for example, alkylphenol polyglycol ethers having linear or branched $C_8$-alkyl residues, commercially available under the name Triton X-100.

In addition, Buffer 2 comprises a complexing reagent, more particularly for divalent metal ions. Suitable for this purpose are all substances which are capable of complexing metal ions and, more particularly, divalent metal ions, for example, DTPA, EGTA or EDTA, with EDTA being preferred.

Optionally, Buffer 2 can additionally comprise a foaming inhibitor in order to prevent, during the mechanical lysis, the sample from excessively foaming, which in extreme cases would lead to unwanted escape of the sample from the sample vessel and thus to substance loss and would, furthermore, also complicate the subsequent processing of the sample, owing to, inter alia, the increase in volume.

For the purposes of the invention, preference is given to, for example, the commercially available foaming inhibitors Reagent DX (QIAGEN, Hilden, Germany) and SILFOAM® SRE (Wacker Chemie, Munich, Germany). If the lysis buffer comprises a foaming inhibitor, this inhibitor is preferably present at a percentage of from 0.1 to 1% (v/v), based on the total composition of the buffer.

Particularly preferably, Buffer 2, which also advantageously exhibits lytic properties, comprises (1) a buffer substance, (2) complexing reagent, (3) surfactant and (4) optionally a foaming inhibitor, such as Reagent DX, and has a pH in the range from 7.0 to 9.0. It is preferred that the respective buffer components, during the mechanical lysis, are present at a concentration of (1) from 2 to 20 mM, preferably from 4 to 15 mM, more preferably from 5 to 10 mM buffer substance, (2) from 0.1 to 5 mM, preferably from 1 to 4 mM, more preferably from 2 to 3 mM complexing reagent, (3) from 0.1 to 5% (w/v), preferably from 1 to 3% (w/v), more preferably from 1.8 to 2% (w/v) surfactant, preferably non-ionic surfactant, and (4) optionally from 0.1 to 1% (v/v), preferably from 0.3 to 0.9% (v/v), more preferably from 0.5 to 0.7% (v/v) foaming inhibitor, preferably at a pH in the range from 7.0 to 9.0, more preferably of 8.0. A suitable buffer solution which delivers lysis conditions of this kind preferably comprises (1) from 5 to 50 mM, preferably from 8 to 25 mM, more preferably from 10 to 20 mM buffer substance, (2) from 0.5 to 10 mM, preferably from 1 to 8 mM, more preferably from 2 to 5 mM complexing agent, (3) from 0.2 to 10% (w/v), preferably from 0.5 to 5% (w/v), more preferably from 1.2 to 2% (w/v) surfactant and (4) optionally from 0.1 to 3% (v/v), preferably from 0.2 to 2% (v/v), more preferably from 0.5 to 1% (v/v) foaming inhibitor, such as, for example, Reagent DX, preferably at a pH in the range from 7.0 to 9.0, more preferably of 8.0.

Since it can occur in practice that the above lysis method does not lead to a complete lysis of the microbial cells, but only to a partial lysis of the microbial cells, there is therefore, in a preferred embodiment, a further, downstream lysis method which is preferably carried out with a lysis solution. It is, however, also possible to directly lyse the microbial cells with the appropriate lysis solution without carrying out mechanical lysis beforehand.

Since it is particularly advantageous for the purification and concentration of particularly the microbial and, if present, viral nucleic acids, to include a protease digestion, this digestion can be conveniently combined with the described lysis step. It is, however, also possible to carry out the protease digestion in another procedural step, for example, in combination with the mechanical lysis, or in the subsequent purification process and/or concentration process.

Advantageously, to optimize the lysis of the microbial cells corresponding to procedural step 5, the lysis is at least partially achieved by adding a protease, preferably proteinase K, and a lysis solution (Buffer 3) to the suspension from procedural step 4 or to the lysate resulting from the above-described prior mechanical lysis, which is supported if appropriate by a likewise at least partially lytic buffer. Buffer 3 preferably comprises 1. at least one chaotropic substance, preferably selected from the group comprising guanidinium thiocyanate (GTC), guanidinium hydrochloride (GuHCl), guanidinium isothiocyanate (GIT), alkali perchlorates, alkali iodides, urea and mixtures thereof,
2. at least one surfactant, preferably a non-ionic surfactant, particularly preferably selected from the group comprising sorbitan esters of fatty acids, polyoxyethylene sorbitan esters of fatty acids, polyoxyalkylene ethers of fatty acid alcohols, polyoxyalkylene ethers of alkylphenols, poloxamers and mixtures thereof and
3. at least one buffer substance, preferably Tris, MES, MOPS, HEPES and mixtures thereof.

The mixture obtained is incubated to activate the protease, preferably for from 5 to 40 minutes at from 45° to 70° C., more preferably for from 10 to 20 minutes at from 50 to 65° C., particularly preferably for 15 minutes at 60° C. Preferably, the sample is to this end admixed with a volume of Buffer 3 which is from 40 to 150%, preferably from 70 to 110% and more particularly 90% of the sample volume, and also a volume of a protease solution, preferably a proteinase K solution having >600 mAU/ml (AU: Anson unit), commercially available, for example, as QIAGEN Proteinase K (QIAGEN, Hilden, Germany), which is from 1 to 30%, preferably from 5 to 20% and particularly preferably 10% of the sample volume. For instance, to 5 ml of the sample in a particularly preferred embodiment there are added 4 ml of Buffer 3 and 0.5 ml of protease solution.

Particularly good results are achieved when the above-mentioned substances of the buffer solution are present during the lysis more particularly at a concentration of (1) from 1 to 5 M chaotrope, (2) from 5 to 20% (w/v) surfactant and (3) from 20 to 100 mM buffer substance, more particularly at pH 8.0.

A suitable buffer which delivers lysis conditions of this kind comprises (1) from 3 to 10 M, preferably from 4 to 8 M, more preferably from 4.5 to 6 M chaotrope, (2) from 10 to 40% (w/v), preferably from 15 to 30% (w/v), more preferably from 20 to 25% (w/v) surfactant and (3) from 40 to 200 mM, preferably from 50 to 150 mM, more preferably from 70 to 100 mM buffer substance, more particularly at pH 8.0.

In a particularly preferred embodiment, the described Buffer 3 was already added to the liquid constituent from procedural step 1.

In a preferred embodiment of the method according to the invention, both the intracellular microbial nucleic acids and the free-circulating, more particularly the extracellular microbial, nucleic acids and, additionally and particularly preferably, viral nucleic acids are accumulated and/or isolated.

For this purpose, the liquid constituent removed in procedural step 1 of the method according to the invention, comprising the free-circulating, more particularly the extracellular microbial, nucleic acids and, if present, the viral nucleic acids, can be combined with the lysate obtained in procedural step 5, comprising the intracellular microbial nucleic acids, prior to the purification and/or concentration of the nucleic acids in procedural step 6 of the method according to the invention. In this case, the liquid constituent removed in procedural step 1 of the method according to the invention, comprising the free-circulating, more particularly extracellular microbial, nucleic acids and, if present, the viral nucleic acids, can preferably be added immediately after its removal to the above-described Buffer 3 and stored therein. The lysate obtained as described above in an optional upstream mechanical lysis step and comprising the intracellular microbial nucleic acids can then be subsequently added, to optimize the lysis, to this mixture.

Alternatively, the liquid constituent obtained in procedural step 1 of the method according to the invention, comprising the free-circulating, more particularly extracellular microbial, nucleic acids and, if present, the viral nucleic acids, and the lysate obtained in procedural step 5, comprising the intracellular microbial nucleic acids, can be purified and/or concentrated independently of one another. If the liquid constituent obtained in procedural step 1 also comprises viruses and isolation of the viral nucleic acids is desired, this liquid constituent is preferably further subjected to an additional step to release the viral nucleic acids. Methods for this purpose are known to a person skilled in the art and typically comprise chemical lysis and/or proteinase digestion.

The protease for the protease digestion, preferably proteinase K, more particularly in the form of a buffer, can either be added both to the suspension from procedural step 4 or to the lysate resulting from the above-described prior mechanical lysis and to the liquid constituent obtained in procedural step 1, in each case in separate sample mixtures. Alternatively, the lysate of the mechanical lysis and the liquid constituent from procedural step 1, optionally in combination with Buffer 3, can be combined prior to the addition of the protease-containing buffer.

It is likewise possible to add the protease-containing buffer only to the lysate of the mechanical lysis. The extracellular nucleic acids from the liquid constituent from procedural step 1 can then be subsequently purified and/or concentrated with the intracellular nucleic acids present in the lysate of the downstream chemical lysis, either together (combined) or independently of one another, according to the further steps 6a-6d described below.

The purification and/or concentration of the microbial and viral nucleic acids in step 6 of the method according to the invention preferably comprises the following steps:

6a) adding to the lysate from procedural step 5 a mixture (binding buffer), preferably comprising a mixture of (1) a linear or branched $C_1$-to-$C_4$ alcohol, more particularly methanol, ethanol, propanol, Isopropanol or n-butanol, isobutanol, sec-butanol or tert-butanol, preferably isopropanol, and (2) a buffer corresponding to Buffer 3, preferably in a ratio of 30-80% by volume of the linear or branched $C_1$-to-$C_4$ alcohol to 20-70% by volume of Buffer 3, and incubating the resulting mixture;

6b) applying the sample to a suitable chromatographic apparatus, preferably to a chromatographic apparatus for selective binding of the microbial and, if present, viral nucleic acids by adsorption, particularly preferably on the basis of silica;

6c) optionally washing one or more times the bound microbial and, if present, viral nucleic acids, preferably with a first solution (Wash Buffer 1) which comprises (1) at least one chaotropic substance, preferably selected from the group comprising guanidinium thiocyanate (GTC), guanidinium hydrochloride (GuHCl), guanidinium isothiocyanate (GIT), alkali perchlorates, alkali iodides and mixtures thereof, (2) a linear or branched $C_1$-$C_4$ alcohol, preferably ethanol, and (3) at least one chaotropic salt, preferably at a concentration in the range from 2 to 4 M, preferably followed by a second solution (Wash Buffer 2) which comprises (1) a linear or branched $C_1$-$C_4$ alcohol, preferably ethanol, (2) a non-chaotropic salt, preferably sodium chloride, at a concentration in the range from 10 to 200 mM and (3) from 1 to 25 mM of a buffer substance, preferably Tris, MES, MOPS, HEPES or mixtures thereof (pH 7.5) but does not comprise any chaotropic substance;

6d) optionally eluting the microbial and, if present, viral nucleic acids, preferably with water or a solution (elution buffer) comprising (1) at least one buffer substance and (2) at least one complexing reagent for metal ions, more particularly for divalent metal ions. Similarly, other conventional elution agents can be used.

The volume of the binding buffer added to the sample is preferably in the range from 100 to 500% of the sample volume, preferably in the range from 200 to 400% of the sample volume and particularly preferably 320% of the sample volume. The resulting mixture is subsequently incubated preferably for from 1 to 20 minutes at −5 to 5° C., particularly preferably for from 2 to 10 minutes at 0° C. and more particularly for 5 minutes at 0° C.

The microbial and, if present, viral nucleic acids obtained are preferably removed from the rest of the sample constituents through selective attachment of the microbial and, if present, viral nucleic acids to a solid matrix by adsorption, preferably by adsorption to a silica-based matrix which, upon addition of a suitable binding buffer, substantially and selectively binds the nucleic acid molecules present in a solution, whereas proteins and further cell constituents and buffer constituents present in the solution, such as salts, buffer substances, surfactants, etc., remain in solution and can be removed from the bound nucleic acids through the wash solution. The terms "selective binding" and "selective attachment" of nucleic acids, for the purposes of the invention, via a matrix is understood to mean, for the purposes of the invention, the specific interaction (chemical or physical binding through complexing, adhesion, etc.) of nucleic acid molecules with the matrix, whereas the matrix does not interact, or interacts to a lesser extent, with further sample constituents which are not nucleic acids, for example, salts, proteins, etc. It is, however, not necessary for the interaction of the matrix with nucleic acids of different origin to differ, i.e. for there to have to be a difference in the type and strength of the interaction with microbial nucleic acids when compared to eukaryotic nucleic acids. Suitable systems are known to a person skilled in the art and commercially available in a multiplicity of configurations, for example, also in formats which selectively bind only the DNA present in a sample, while the RNA molecules present in the sample, and also the proteins and the further sample constituents and buffer constituents present in the sample remain in solution. Formats of this kind are particularly preferred when only DNA, but no RNA, is to be isolated. Particularly preferable for the purposes of the invention are, for example, QIAamp DNA Mini columns or the QIAamp Mini columns present in the QIAamp Circulating Nucleic Acid Kit (Qiagen, Hilden, Germany), which are preferably in the form of a spin column in which washing and elution can be carried out simply and quickly by centrifugation or application of vacuum. The volume of Wash Buffers 1 and 2 used for optional washing of the bound microbial and, if present, viral nucleic acids is a function of the size and dimension of the chromatographic apparatus used in step 6b and also the amount of sample applied. Corresponding information can be found in the protocols of the respective manufacturer. In the case of a QIAamp DNA Mini column, the preferred volume of Wash Solutions 1 and 2 is, for example, in the range from 500 to 900 µl for purification of a sample which was acquired from an original sample volume of 10 ml of human whole blood.

Preferably, the column is dried after washing the bound nucleic acids before the nucleic acids can be optionally eluted from the column in step 6d) of the method according to the invention. For this purpose, the column can be rinsed with, for example, from 500 to 900 µl of ethanol, subsequently centrifuged at maximum speed and then dried at room temperature or at an elevated temperature (from 40 to 65° C.).

The elution buffer optionally used in step 6d) of the method according to the invention preferably comprises Tris-HCl and EDTA, particularly preferably from 2 to 20 mM Tris-HCl and from 0.1 to 1 mM EDTA, more particularly 10 mM Tris-HCl and 0.5 mM EDTA. The volume of the elution buffer too is a function of both the type and dimension of the chromatographic apparatus and the amount of sample applied to the chromatographic apparatus. Preferred values can be found in, for example, the instructions of the manufacturer of the chromatographic apparatus. In the case of use of a QIAamp DNA Mini column and a starting sample amount of about 10 ml of whole blood, the volume of the elution buffer is preferably from 20 to 200 µl. Preferably, the column is briefly incubated at room temperature (from about 1 to 5 minutes) after addition of the elution buffer before the nucleic acids are eluted by centrifugation at maximum speed, for example, from 0.5 to 3 minutes at 20,000 g.

Generally, it is, however, also possible to further process and/or analyse the bound nucleic acid without prior elution.

The present invention further provides a kit for selectively accumulating and/or isolating intracellular microbial and also free-circulating, more particularly extracellular microbial, nucleic acids and also any additional viral nucleic acids from samples which comprise a mixture of microbial and higher eukaryotic cells and free-circulating nucleic acids, more particularly extracellular microbial nucleic acids, and also, possibly and additionally, viruses in a liquid, comprising:

1. a first buffer, preferably having lytic properties (Buffer 1), said buffer having already been described in detail above,
2. at least a second buffer (Buffer 2), preferably having lytic properties, and/or a further buffer (Buffer 3), preferably having lytic properties, said buffers having likewise already been described in detail above, and
3. glass beads, preferably having a diameter in the range from 400 to 600 µm, particularly preferably having a diameter of 500 µm.

In a preferred embodiment, the kit further comprises a chromatographic apparatus for purifying and/or concentrating the microbial and, if present, viral nucleic acids, preferably a chromatographic apparatus for selective binding of DNA and/or RNA by adsorption, particularly preferably on the basis of silica, and also a binding buffer, preferably the already defined binding buffer, optionally one or more wash buffers, preferably the two wash buffers already defined above and optionally an elution buffer, preferably the elution buffer already defined above. Optionally, the kit can further comprise components for detecting the accumulated and/or isolated nucleic acids in a multiplex assay, for example, multiple primer pairs, a suitable DNA polymerase, deoxyribonucleoside triphosphates, a source of $Mg^{2+}$ ions and/or buffer solutions suitable for PCR, for detection of the DNA obtained in a multiplex PCR.

EXAMPLES

Example 1

Selective Accumulation and Isolation of Fungal DNA from Whole Blood Samples

Whole blood was spiked with free *Aspergillus* DNA ($1\times10^4$ genome equivalents/ml of whole blood) and cells of *C. albicans* and *I. orientalis* (in each case, $1\times10^4$ cells/ml of whole blood). To isolate the fungal DNA, portions of the spiked blood were processed in, in total, four different ways A to D:

A (comparative method without depletion of the human nucleic acids and without a mechanical pre-lysis step): 500 µl of the spiked whole blood received the addition of and was commixed with 250 µl of a Lysis Buffer 2, comprising 20 mM Tris-HC1, 2 mM EDTA, 1.2% Triton X-100 and 0.5% Reagent DX. The mixture obtained received the addition of 500 µl of the commercially available Lysis Buffer AL (QIAGEN, Hilden, Germany) and also 50 µl of Qiagen Proteinase K and was incubated for 10 min at 56° C. Subsequently, the nucleic acids were isolated using the QIAamp Blood Mini Kit (QIAGEN, Hilden, Germany) according to the manufacturer's instructions using the mini columns and wash and elution buffers present in the kit, with the nucleic acids bound to the columns being washed with 750 µl each of Buffer AW1 and Buffer AW2 and eluted with 50 µl of Buffer AE.

B (comparative method without depletion of the human nucleic acids): 1 ml of the spiked whole blood received the addition of 500 µl of Lysis Buffer 2 and also 800 mg of glass beads of a diameter of 500 µm and was commixed for 10 min by vortexing to achieve mechanical disruption. 500 µl of the mixture obtained received the addition of 500 µl A of the commercially available Lysis Buffer AL (QIAGEN, Hilden, Germany) and also 50 µl of Qiagen Proteinase K and were incubated for 10 min at 56° C. Subsequently, the nucleic acids were isolated using the QIAamp Blood Mini Kit (QIAGEN, Hilden, Germany) according to the manufacturer's instructions using the mini columns and wash and elution buffers present in the kit, with the nucleic acids bound to the columns being washed with 750 µl each of Buffer AW1 and Buffer AW2 and eluted with 50 µl of Buffer AE.

C: 5 ml of the spiked whole blood received the addition of 1.9 ml of a Lysis Buffer 1, comprising 1.5 M GTC, 6.7% Brij 58 and 33 mM Tris (pH 8), and the mixture was incubated for 10 min at room temperature and subsequently centrifuged for 10 min at 5000 rpm. The supernatant obtained after centrifugation was discarded, leaving a volume of about 50 µl. The remaining pellet was resuspended in about 450 µl of PBS buffer (comprising 137 mM sodium chloride, 2.7 mM potassium chloride and 12 mM total phosphate of disodium hydrogen phosphate and potassium dihydrogen phosphate). The mixture obtained (about 500 µl) was transferred to a new vessel containing 250 µl of Lysis Buffer 2 and 400 mg of glass beads of a diameter of about 425-600 µm. The sample was mixed for 10 min by vortexing to achieve mechanical disruption. 500 µl of the supernatant obtained received the addition of 500 µl of the commercially available Lysis Buffer AL (QIAGEN, Hilden, Germany) and also 50 µl of Qiagen Proteinase K and were incubated for 10 min at 56° C. Subsequently, the nucleic acids were isolated using the QIAamp Blood Mini Kit (QIAGEN, Hilden, Germany) according to the manufacturer's instructions using the mini columns, wash and elution buffers present in the kit, with the nucleic acids bound to the columns being washed with 750 µl each of Buffer AW1 and Buffer AW2 and eluted, after drying the column, with 50 µl of Buffer AE.

Figure 1:
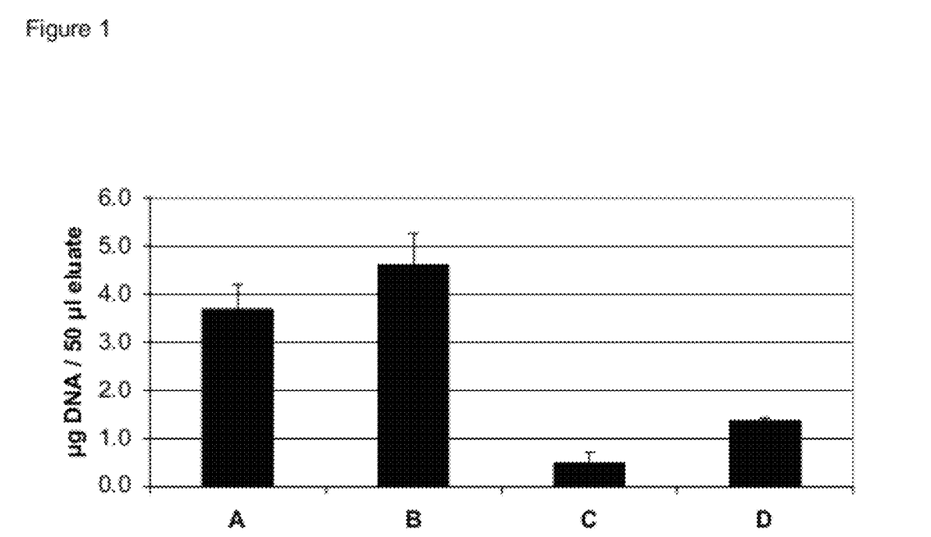
FIG. 1 shows the total amount of DNA obtained (i.e. the sum of human and fungal DNA, with the human DNA representing the main proportion) which was acquired in four different methods A to D (see Example 1) from human whole blood samples spiked with isolated fungal DNA and fungal cells (free *Aspergillus* DNA and also cells of *C. albicans* and *I. orientalis*). The sample amount underlying Sample A was 500 µl of whole blood; for Sample B, 1 ml of whole blood was used. For Samples C and D, the starting sample amount was 5 and 10 ml, respectively, of whole blood, where, for Sample C, only the solid sample constituents remaining after removal of the liquid constituents (blood plasma) were processed and purified with depletion of human nucleic acids, while, for Sample D prior to the chromatographic purification, the lysed microbial cells were combined with the liquid constituent of the sample, comprising the extracellular microbial nucleic acids and removed in step 1 of the method according to the invention. While Samples A and B were treated by means of conventional methods without depletion of the human gDNA and therefore have a high content of human gDNA, the content of human gDNA in Samples C and D is distinctly lower, although the sample volume of Samples C and D was 5 to 20 times the sample volume of Samples A and B.
Figure 2:
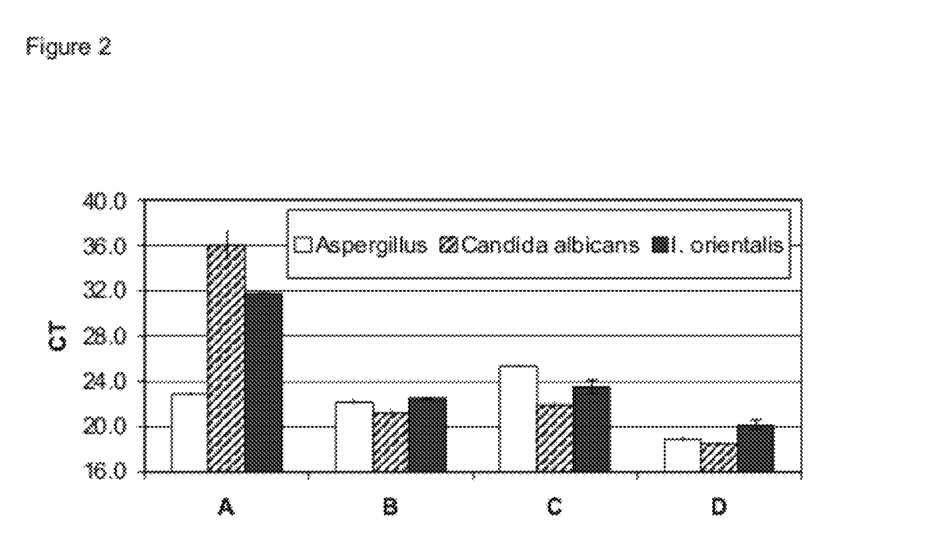
FIG. 2 shows the result of the multiplication of the microbial DNA of Samples A to D shown in FIG. 1 by means of multiplex real-time PCR, in terms of the CT values obtained (see Example 1).

D (method according to the invention):

10 ml of the spiked whole blood were centrifuged for 10 minutes at about 5000 g to remove the blood plasma, including the extracellular nucleic acids present in the blood plasma. After centrifugation was carried out, the upper plasma phase (about 4.5 ml) was removed and transferred to a new vessel. The volume of the solid constituents was made up to 10 ml by the addition of PBS buffer. After the addition of 3.75 ml of Lysis Buffer 1, the mixture obtained was incubated for 10 min at room temperature. The mild lysis buffer lyses only the human cells, whereas the microbial cells remain intact. Subsequently, the sample was centrifuged for 15 min at about 5000 rpm. The supernatant obtained was removed, leaving a volume of 250 µl A, and discarded. This supernatant comprises, in particular, human DNA and can alternatively also be further used for a separate differential nucleic acid purification procedure. The remaing pellet received the addition of 250 µl each of PBS buffer and Lysis Buffer 2. 400 mg of glass beads of a size of 425-600 µl µm were added, and the mixture was commixed for 10 min by vortexing or using the QIAGEN TissueLyser LT at 50 Hz to achieve mechanical disruption. 500 µl of the supernatant were added to the previously removed plasma fraction (it is also possible to filter the mechanically disrupted mixture of sample and glass beads via a coarse filter directly into the plasma fraction in order to minimize the loss of liquid sample material) and received the addition of 4 ml of Lysis Buffer 3, comprising 4.5 M GTC, 20% Brij 58 and 100 mM Tris (pH 8), and 500 µl of QIAGEN Proteinase K. The mixture obtained was incubated for 20 min at 60° C., received the addition of 9 ml of a binding buffer comprising 1.2 M GTC, 5.5% Brij 58, 27.6 mM Tris and 72% (v/v) isopropanol, was commixed by vortexing and was incubated for 5 min on ice. The sample was subsequently drawn under vacuum onto a QIAamp Mini column with the help of an attachment which allows sample volumes which are greater than the volume of the sample itself to be applied to a column, for example a 20 ml Extender (QIAgen, Hilden, Germany), and the nucleic acids present in the sample were selectively bound to the column. The nucleic acids bound to the columns were then washed with 750 µl each of the commercially available Buffer AW1 and Buffer AW2 (QIAGEN, Hilden, Germany), the column was dried and the nucleic acids were eluted with 50 µl of the commercially available Buffer AE (QIAGEN, Hilden, Germany). The total amount of DNA (human and fungal DNA) in the eluate was determined by means of UV-Vis spectroscopy (FIG. 1). To detect the fungal DNA, 8 µl of each purified sample were taken and subjected to multiplex PCR. The results are depicted in FIG. 2.

Example 2

Selective Accumulation and Isolation of Bacterial DNA from Whole Blood Samples

Figure 3:
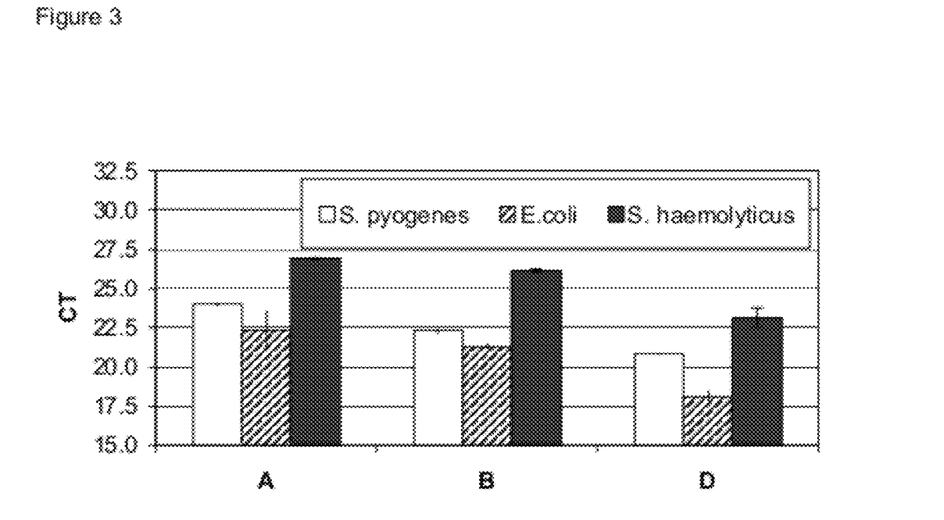
FIG. 3 shows the result of the multiplication of bacterial DNA by means of multiplex real-time PCR, with the DNA having been acquired in three different methods A, B and D (see Example 2) from human whole blood samples spiked with isolated bacterial DNA and bacterial cells (free *S. haemolyticus* DNA and also cells of *E. coli* and *S. pyogenes*). The sample amount underlying Sample A was 500 µl of whole blood; for Sample B, 1 ml of whole blood was used. For Sample D, the starting sample amount was 10 ml of whole blood, where prior to the chromatographic purification, the lysed microbial cells were combined with the liquid constituent of the sample, comprising the extracellular microbial nucleic acids and removed in step 1 of the method according to the invention. The CT value of Sample D treated according to the invention is also in the case of isolation of bacterial DNA distinctly lower.

Whole blood was spiked with free S. haemolyticus DNA ($1\times10^4$ genome equivalents/ml of whole blood) and the cells of E. coli and S. pyogenes (in each case, $1\times10^4$ cells/ml of whole blood). To isolate the bacterial DNA, portions of the spiked blood were processed in, in total, three different ways A, B and D, as described in Example 1. To detect the bacterial DNA, 7.5 µl of each purified sample were taken and subjected to multiplex PCR. The results are depicted in FIG. 3.

Example 3

Selective Accumulation and Isolation of Viral Nucleic Acids from Whole Blood Samples Human whole blood was spiked with commercially available HBV and HCV standards (Acrometrix, Benicia, Calif., USA) such that, in each case, a virus concentration of $5.0\times10^4$ IU/ml (International Units per millilitre) in the blood sample was obtained.

Figure 4:
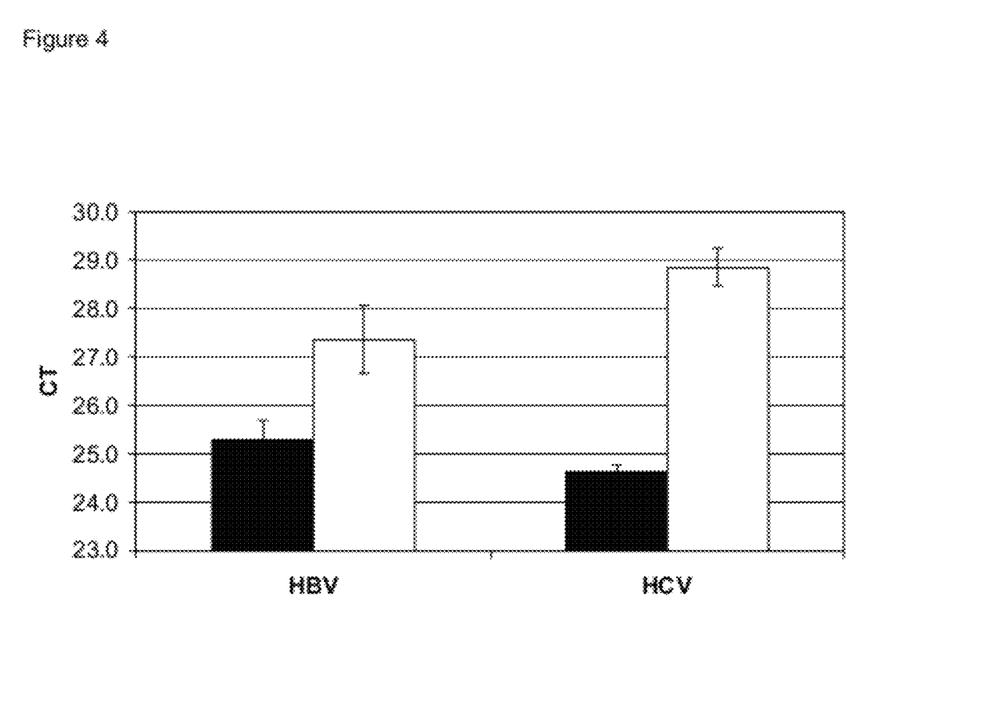
FIG. 4 shows the result of the multiplication of viral nucleic acids obtained using the method according to the invention (displayed as black bars) by means of multiplex real-time PCR or multiplex real-time reverse-transcriptase PCR in comparison with nucleic acids which were acquired using a commercially available kit for detecting viral nucleic acids (white bars), for deoxyribonucleic acids on the basis of hepatitis B viruses (HBV) and ribonucleic acids on the basis of hepatitis C viruses (HCV) (see Example 3).

To isolate the viral nucleic acids, the samples were processed in two different ways: In one case, 500 µl of blood plasma, which was obtained by centrifugation of a portion of the spiked blood, were processed using the commercially available QIAGEN DSP Virus Kit (QIAGEN, Hilden, Germany) according to the manufacturer's instructions. In the other case, 8 ml of the spiked whole blood were processed in accordance with the method according to the invention, as described under D in Example 1. The detection and the quantification of the viral nucleic acids obtained were performed by means of real-time PCR and real-time reverse-transcriptase PCR. The results are depicted in FIG. 4.

Example 4

Isolation of Microbial Nucleic Acids Using Different Isopropanol Concentrations in the Binding Buffer Human whole blood was spiked either with free DNA of *Aspergillus fumigatus* and *Candida albicans* or with live cells of *S. pyogenes* and *E. coli*. Firstly, the gDNA from the human blood cells was depleted from these samples in accordance with the method according to the invention described above under D, and the microbial cells in the samples which contained them were disrupted as described above. To the combined plasma fractions (5 ml total in each case) were added, in each case, 4 ml of lysis buffer 3 and 0.5 ml of proteinase K solution. The mixture obtained was incubated at 60° C. for 20 min, received the addition of 9 ml of a binding buffer comprising 1.2 M GTC, 5.5% Brij 58, 27.6 mM Tris and isopropanol, commixed by vortexing, and incubated on ice for 5 min, with the binding buffer having an isopropanol concentration which brought about an isopropanol concentration of about 19.5% or about 42% isopropanol in the binding mixture. (The binding buffer comprised, in each case, at first 5.4 ml of the lysis buffer, 1.2 M GTC, 5.5% Brij 58, 27.6 mM Tris and 3.6 ml isopropanol. For the mixture with an increased isopropanol concentration, an additional 7 ml of isopropanol were added to the mixture). The samples were further processed as described above.

Figure 5:
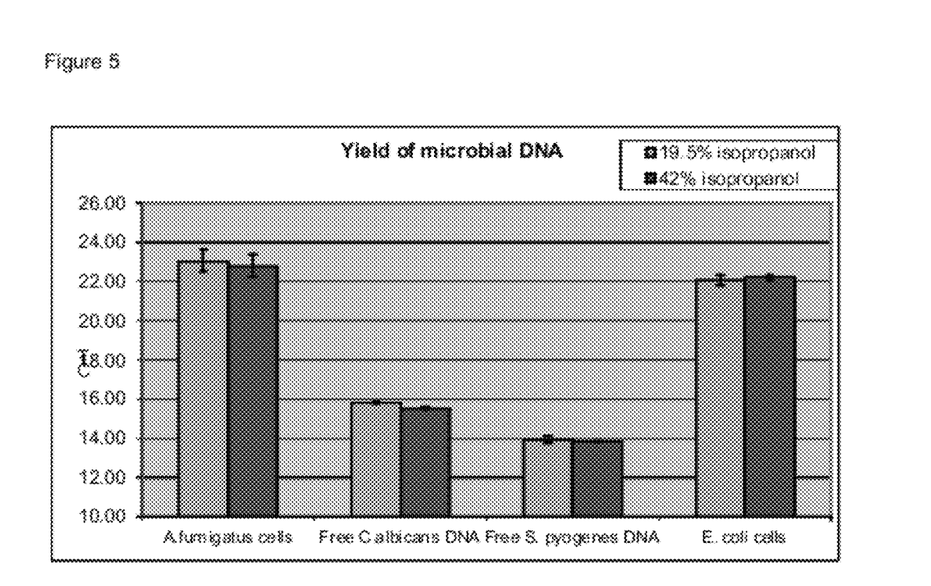
FIG. 5 shows the result of the multiplication of the microbial DNA of the samples processed in Example 4 by means of multiplex real-time PCR, in terms of the CT values obtained (see Example 4). The first pair of bars shows the obtained CT values of the isolated DNA from whole *A. fumigatus* cells, the second pair of bars shows the CT values of the isolated DNA from *C. albicans* (free DNA), the third pair of bars shows CT values of the isolated DNA from *S. pyogenes* (free DNA) and the right-hand pair of bars shows the CT values of the isolated DNA from whole *E. coli* cells. In each case, the left-hand bar shows the result in the case of 19.5% isopropanol and the right-hand bar shows the result in the case of 42% isopropanol.

To detect and to quantify the microbial nucleic acids obtained, 7.5 µl were taken from each purified sample and subjected to multiplex PCR. The results can be seen in Table 1 and FIG. 5. The flow-through times of the samples through the silica columns were 10.5 min in the case of 19.5% isopropanol and 6.5 min in the case of 42% isopropanol.

TABLE 1

| Sample | Mean CT values | | | |
|---|---|---|---|---|
| | A. fumigatus cells | Free C. albicans DNA | Free S. pyogenes DNA | E. coli cells |
| 19.5% isopropanol | 23.04 ± 0.57 | 15.81 ± 0.07 | 13.93 ± 0.16 | 22.06 ± 0.29 |
| 42% isopropanol | 22.80 ± 0.60 | 15.53 ± 0.08 | 13.84 ± 0.02 | 22.20 ± 0.16 |

The invention claimed is:

1. A method for selectively accumulating or isolating microbial nucleic acids and viral nucleic acids from a sample that comprises a mixture of microbial cells, higher eukaryotic cells, free-circulating nucleic acids, and viruses in a liquid, comprising:
   (1) substantially separating the liquid of the sample, including the free-circulating nucleic acids dissolved in the liquid and viruses, from the microbial cells and higher eukaryotic cells of the sample,
   (2) selectively lysing the eukaryotic cells from step (1), leaving the microbial cells intact,
   (3) substantially separating the eukaryotic lysate from step (2) from the intact microbial cells,
   (4) resuspending the intact microbial cells obtained in step (3),
   (5) lysing the microbial cells which are present in the suspension obtained in step (4), and
   (6) purifying or concentrating the free-circulating nucleic acids from the liquid obtained in step (1), viral nucleic acids from the viruses in the liquid obtained in step (1), and the intracellular microbial nucleic acids from the lysate obtained in step (5).

2. The method according to claim 1, wherein the free-circulating nucleic acids are extracellular microbial nucleic acids.

3. A method for selectively accumulating or isolating microbial nucleic acids and free-circulating nucleic acids from a sample that comprises a mixture of microbial cells, higher eukaryotic cells, free-circulating nucleic acids, and optionally viruses in a liquid, comprising:
   (1) substantially separating the liquid of the sample, including the free-circulating nucleic acids dissolved in the liquid and optionally viruses, from the microbial cells and higher eukaryotic cells of the sample,
   (2) selectively lysing the eukaryotic cells from step (1), leaving the microbial cells intact,
   (3) substantially separating the eukaryotic lysate obtained in step (2) from the intact microbial cells,
   (4) resuspending the intact microbial cells obtained in step (3),
   (5) lysing the microbial cells which are present in the suspension obtained in step (4), and
   (6) purifying or concentrating the free-circulating nucleic acids from the liquid obtained in step (1), viral nucleic acids if present in the liquid obtained in step (1), and intracellular microbial nucleic acids from the lysate obtained in step (5) by selectively binding the nucleic acids to a solid matrix.

4. The method according to claim 3, wherein the free-circulating nucleic acids comprise extracellular microbial nucleic acids.

5. The method according to claim 3, wherein the higher eukaryotic cells are mammalian cells.

6. The method according to claim 5, wherein the mammalian cells are human cells.

7. The method of claim 3, wherein the sample is blood or blood concentrate.

8. The method of claim 3, wherein the microbial cells are bacterial cells, fungal cells, protozoan cells, or a mixture of bacterial cells and fungal cells.

9. The method of claim 3, wherein the step (1), step (3), or both steps (1) and (3) are achieved by means of centrifugation, filtration and/or decantation of the sample.

10. The method according to claim 3, wherein the selective lysis of the eukaryotic cells according to step (2) is carried out in a first buffer solution (Buffer 1) that comprises:
    (i) at least one chaotropic substance,
    (ii) at least one surfactant, and
    (iii) at least one buffer substance,
    such that the concentration of these substances in the sample after addition of Buffer 1 is from 0.1 to 2 M chaotropic substance, from 0.5 to 5% (w/v) surfactant, and from 2 to 50 mM buffer substance.

11. The method according to claim 10, wherein the at least one chaotropic substance of Buffer 1 is selected from the group consisting of guanidinium thiocyanate (GTC), guanidinium hydrochloride (GuHC1), guanidinium isothiocyanate (GIT), alkali perchlorates, alkali iodides, urea, and mixtures thereof.

12. The method according to claim 10, wherein the at least one surfactant of Buffer 1 is a non-ionic surfactant.

13. The method according to claim 12, wherein the non-ionic surfactant is selected from the group consisting of sorbitan esters of fatty acids, polyoxyethylene sorbitan esters of fatty acids, polyoxyalkylene ethers of fatty acid alcohols, polyoxyalkylene ethers of alkylphenols, poloxamers, and mixtures thereof.

14. The method according to claim 10, wherein the at least one buffer substance of Buffer 1 is selected from the group consisting of Tris, MES, MOPS, HEPES, and mixtures thereof.

15. The method according to claim 10, wherein the concentration of the at least one buffer substance in the sample after addition of Buffer 1 is from 4 to 10 mM.

16. The method according to claim 10, wherein the pH of Buffer 1 is 8.0.

17. The method according to claim 3, wherein the lysis of the microbial cells in step (5) is at least in part carried out mechanically in the presence of a second buffer solution (Buffer 2).

18. The method according to claim 17, wherein the Buffer 2
    (a) comprises:
       (i) at least one buffer substance,
       (ii) at least one complexing reagent for metal ions, and
       (iii) at least one surfactant, and
    (b) has a pH of from 6 to 10, and
    wherein the substances of the buffer solution are present at a concentration of from 2 to 20 mM buffer substance, from 0.1 to 5 mM complexing reagent, and from 0.1 to 5% (w/v) surfactant, and at pH 8.0 during mechanical lysis.

19. The method according to claim 18, wherein the at least one buffer substance of Buffer 2 is selected from the group consisting of Tris, MES, MOPS, HEPES, and mixtures thereof.

20. The method according to claim 18, wherein the at least one complexing reagent for metal ions of Buffer 2 is a complexing reagent for divalent metal ions.

21. The method according to claim 20, wherein the at least one complexing reagent for metal ions of Buffer 2 is EDTA.

22. The method according to claim 18, wherein the at least one surfactant of Buffer 2 is a non-ionic surfactant.

23. The method according to claim 22, wherein the non-ionic surfactant is selected from the group consisting of sorbitan esters of fatty acids, polyoxyethylene sorbitan esters of fatty acids, polyoxyalkylene ethers of fatty acid alcohols, polyoxyalkylene ethers of alkylphenols, poloxamers, and mixtures thereof.

24. The method according to claim 18, wherein the Buffer 2 has a pH of from 7.0 to 9.0.

25. The method of claim 18, wherein the Buffer 2 further comprises
    (iv) a foaming inhibitor at a concentration of 0.1 to 1% (v/v).

26. The method according to claim 25, wherein the foaming inhibitor of Buffer 2 is Reagent DX or SILFOAM SRE.

27. The method according to claim 3, wherein the lysis of the microbial cells in step (5) is at least in part carried out by mechanical homogenization of the sample using particles in the presence of a second buffer solution (Buffer 2).

28. The method according to claim 27, wherein the particles are glass beads.

29. The method according to claim 28, wherein the size range of the glass beads is from 400 to 600 μm.

30. The method according to claim 3, wherein the lysis of the microbial cells in step (5) is at least in part carried out by adding to the suspension from step (4) a proteinase and a third buffer solution (Buffer 3) that comprises:
    (i) at least one chaotropic substance,
    (ii) at least one surfactant, and
    (iii) at least one buffer substance,
    and wherein the substances of the buffer solution are present at a concentration of from 1 to 5 M chaotropic substance, from 5 to 20% (w/v) surfactant, and from 20 to 100 mM buffer substance.

31. The method according to claim 30, wherein the proteinase is proteinase K.

32. The method according to claim 30, wherein the at least one chaotropic substance of is selected from the group consisting of guanidinium thiocyanate (GTC), guanidinium hydrochloride (GuHC1), guanidinium isothiocyanate (GIT), alkali perchlorates, alkali iodides, urea, and mixtures thereof.

33. The method according to claim 30, wherein the at least one surfactant of Buffer 3 is a non-ionic surfactant.

34. The method according to claim 33, wherein the non-ionic surfactant is selected from the group consisting of sorbitan esters of fatty acids, polyoxyethylene sorbitan esters of fatty acids, polyoxyalkylene ethers of fatty acid alcohols, polyoxyalkylene ethers of alkylphenols, poloxamers, and mixtures thereof.

35. The method according to claim 30, wherein the at least one buffer substance of Buffer 3 is selected from the group consisting of Tris, MES, MOPS, HEPES, and mixtures thereof.

36. The method according to claim 30, wherein the substances of Buffer 3 are present at pH 8.0 during the lysis and incubation of the mixture obtained.

37. The method according to claim 3, wherein the lysis of the microbial cells in step (5) is at least in part carried out mechanically in a second buffer solution (Buffer 2) followed by adding to the lysate resulting from the mechanical lysis a proteinase and a third buffer solution (Buffer 3) that comprises:
    (i) at least one chaotropic substance,
    (ii) at least one surfactant, and
    (iii) at least one buffer substance, and
    wherein the substances of Buffer 3 are present at a concentration of from 1 to 5 M chaotropic substance, from 5 to 20% (w/v) surfactant, and from 20 to 100 mM buffer substance.

38. The method according to claim 37, wherein the Buffer 2
    (a) comprises:
        (i) at least one buffer substance,
        (ii) at least one complexing reagent for metal ions,
        (iii) at least one surfactant, and
    (b) has a pH of from 6 to 10, and
    wherein the substances of Buffer 2 are present at a concentration of from 2 to 20 mM buffer substance, from 0.1 to 5 mM complexing reagent, and from 0.1 to 5% (w/v) surfactant, and at pH 8.0 during mechanical lysis.

39. The method of claim 38, wherein the Buffer 2 further comprises a foaming inhibitor at a concentration from 0.1 to 1% (v/v).

40. The method according to claim 3, wherein the liquid removed in step (1) is combined with the lysate obtained in step (5) prior to the purification or concentration of the nucleic acids according to step (6).

41. The method according to claim 3, wherein nucleic acids in the liquid obtained in step (1) and nucleic acids in the lysate obtained in step (5) are purified or concentrated independently of one another.

42. The method according to claim 3, wherein the selective binding of nucleic acids to the solid matrix in step (6) is carried out in the presence of a binding buffer, wherein the binding buffer comprises a mixture of (a) a linear or branched $C_1$-to-$C_4$ alcohol, and (b) Buffer 3 that comprises from 3 to 6 M chaotrope, from 10 to 30% (w/v) surfactant, and from 50 to 150 mM buffer substance.

43. The method according to claim 42, wherein the pH of the binding buffer is 8.0.

44. The method according to claim 42, wherein the linear or branched $C_1$-to-$C_4$ alcohol is isopropanol.

45. The method according to claim 3, wherein the binding buffer comprises the linear or branched $C_1$-to-$C_4$ alcohol and Buffer 3 in a ratio of 30-80% to 20-70%.

46. The method according to claim 3, wherein the solid matrix is comprised in a chromatographic apparatus.

47. The method according to claim 46, wherein the solid matrix a silica-based matrix.

48. The method according to claim 46, wherein step (6) comprises:
    (6a) adding to the lysate from step (5) and to the liquid from step (1) a binding buffer, and incubating the resulting mixture, and
    (6b) applying the mixture of step (6a) to the solid matrix comprised in the chromatographic apparatus.

49. The method of claim 3, wherein the purification or concentration of the microbial nucleic acids, and if present, viral nucleic acids, according to step (6) further comprises:
    washing one or more times microbial nucleic acids and if present, viral nucleic acids, that are bound to the solid matrix.

50. The method of claim 49, whether the purification or concentration of the microbial nucleic acids, and if present, viral nucleic acids, according to step (6) further comprises:
    eluting the microbial nucleic acids and viral nucleic acids, if present, from the solid matrix.

51. The method of claim 3, whether the purification or concentration of the microbial nucleic acids, and if present, viral nucleic acids, according to step (6) further comprises:

eluting the microbial nucleic acids and viral nucleic acids, if present, from the solid matrix.

52. A method for selectively accumulating or isolating microbial nucleic acids from a sample that comprises a mixture of microbial cells, higher eukaryotic cells and free-circulating nucleic acids in a liquid, comprising:
   (1) substantially separating the liquid of the sample, including the free-circulating nucleic acids dissolved in the liquid, from the microbial cells and higher eukaryotic cells of the sample,
   (2) selectively lysing the eukaryotic cells from step (1), leaving the microbial cells intact,
   (3) substantially separating the eukaryotic lysate obtained in step (2) from the intact microbial cells,
   (4) resuspending the microbial cells obtained in step (3),
   (5) lysing the microbial cells which are present in the suspension obtained in step (4), wherein the lysis of the microbial cells is at least in part carried out by adding to the suspension from step (4) a proteinase and a third buffer solution (Buffer 3) that comprises:
     (i) at least one chaotropic substance,
     (ii) at least one surfactant, and
     (iii) at least one buffer substance,
     wherein the substances of the buffer solution are present at a concentration of from 1 to 5 M chaotropic substance, from 5 to 20% (w/v) surfactant, and from 20 to 100 mM buffer substance, and
   (6) purifying or concentrating the free-circulating nucleic acids from the liquid obtained in step (1) and intracellular microbial nucleic acids from the lysate obtained in step (5).

53. The method of claim 52, wherein the lysis of the microbial cells in step (5) is at least in part carried out mechanically in a second buffer solution (Buffer 2) prior to adding the proteinase and the Buffer 3.

* * * * *

UNITED STATES PATENT AND TRADEMARK OFFICE
CERTIFICATE OF CORRECTION

| | |
|---|---|
| PATENT NO. | : 9,012,146 B2 |
| APPLICATION NO. | : 13/510525 |
| DATED | : April 21, 2015 |
| INVENTOR(S) | : Dirk Heckel et al. |

Page 1 of 1

It is certified that error appears in the above-identified patent and that said Letters Patent is hereby corrected as shown below:

In the Claims

Column 21, Line 43:
"one chaotropic substance of is selected from the group" should read, --one chaotropic substance of Buffer 3 is selected from the group--.

Signed and Sealed this
First Day of December, 2015

Michelle K. Lee
*Director of the United States Patent and Trademark Office*